(12) United States Patent
Ignon

(10) Patent No.: US 10,238,812 B2
(45) Date of Patent: Mar. 26, 2019

(54) SKIN TREATMENT SYSTEMS AND METHODS USING NEEDLES

(71) Applicant: EDGE SYSTEMS LLC, Signal Hill, CA (US)

(72) Inventor: Roger Ignon, Redondo Beach, CA (US)

(73) Assignee: Edge Systems LLC, Long Beach, CA (US)

( * ) Notice: Subject to any disclaimer, the term of this patent is extended or adjusted under 35 U.S.C. 154(b) by 0 days.

(21) Appl. No.: 14/211,089

(22) Filed: Mar. 14, 2014

(65) Prior Publication Data
US 2014/0343481 A1  Nov. 20, 2014

Related U.S. Application Data

(60) Provisional application No. 61/788,420, filed on Mar. 15, 2013.

(51) Int. Cl.
*A61M 5/32* (2006.01)
*A61B 17/54* (2006.01)
(Continued)

(52) U.S. Cl.
CPC ......... *A61M 5/3298* (2013.01); *A61B 17/205* (2013.01); *A61B 17/545* (2013.01);
(Continued)

(58) Field of Classification Search
CPC .............. A61M 1/0084; A61M 5/3298; A61M 5/3295; A61M 2037/0007;
(Continued)

(56) References Cited

U.S. PATENT DOCUMENTS

| 1,651,585 A | 12/1927 | Clair |
| 2,608,032 A | 8/1952 | Garver |

(Continued)

FOREIGN PATENT DOCUMENTS

| AT | 400 305 | 12/1995 |
| AU | 1 014 299 | 5/1999 |

(Continued)

OTHER PUBLICATIONS

International Search Report and Written Opinion for PCT/US14/24992 dated Jul. 21, 2014 for related application.
(Continued)

*Primary Examiner* — Emily L Schmidt
*Assistant Examiner* — Leah J Swanson
(74) *Attorney, Agent, or Firm* — Knobbe Martens Olson & Bear, LLP

(57) ABSTRACT

A device for treating the skin comprises a handpiece assembly having a distal end and a proximal end and a tip on the distal end of the handpiece assembly. The handpiece assembly includes a fluid delivery conduit, a waste conduit and/or an energy delivery conduit. Further, the tip is configured to contact the skin. The tip comprises a peripheral lip and a plurality of needles generally positioned within the peripheral lip. The tip also comprises at least one opening in fluid communication with a fluid delivery conduit, at least one opening in fluid communication with a waste conduit and/or an energy contact point in electrical communication with an energy contact point and energy conduit in the main body portion. The plurality of needles may be movable with respect to the peripheral lip through the use of a pneumatic or other force.

17 Claims, 11 Drawing Sheets

(51) Int. Cl.
*A61B 17/20* (2006.01)
*A61M 37/00* (2006.01)
*A61B 17/00* (2006.01)

(52) U.S. Cl.
CPC .............. *A61B 2017/00747* (2013.01); *A61M 37/0015* (2013.01); *A61M 2037/0007* (2013.01); *A61M 2202/07* (2013.01); *A61M 2202/095* (2013.01)

(58) Field of Classification Search
CPC ...... A61M 37/0015; A61M 2037/0023; A61M 2037/003; A61M 2037/0046; A61M 2037/0061
USPC ..................................................... 604/21, 22
See application file for complete search history.

(56) References Cited

U.S. PATENT DOCUMENTS

| | | |
|---|---|---|
| 2,631,583 A | 3/1953 | Lavergne |
| 2,701,559 A | 2/1955 | Cooper |
| 2,712,823 A | 7/1955 | Kurtin |
| 2,867,214 A | 1/1959 | Wilson |
| 2,881,763 A | 4/1959 | Robbins |
| 2,921,585 A | 1/1960 | Schumann |
| 3,037,509 A | 6/1962 | Schutz |
| 3,085,573 A | 4/1963 | Meyer et al. |
| 3,214,869 A | 11/1965 | Stryker |
| 3,468,079 A | 9/1969 | Kaufman |
| 3,476,112 A | 11/1969 | Elstein |
| 3,481,677 A | 12/1969 | Abrahamson |
| 3,505,993 A | 4/1970 | Lewes et al. |
| 3,574,239 A | 4/1971 | Sollerud |
| 3,715,838 A | 2/1973 | Young et al. |
| 3,865,352 A | 2/1975 | Nelson et al. |
| 3,866,264 A | 2/1975 | Engquist |
| 3,948,265 A | 4/1976 | Al Ani |
| 3,964,212 A | 6/1976 | Karden |
| 3,968,789 A | 7/1976 | Simoncini |
| 3,977,084 A | 8/1976 | Sloan |
| 4,121,388 A | 10/1978 | Wilson |
| 4,155,721 A | 5/1979 | Fletcher |
| 4,170,821 A | 10/1979 | Booth |
| 4,182,329 A | 1/1980 | Smit et al. |
| 4,203,431 A | 5/1980 | Abura et al. |
| 4,216,233 A | 8/1980 | Stein |
| 4,225,254 A | 9/1980 | Holberg et al. |
| 4,289,158 A | 9/1981 | Nehring |
| 4,299,219 A | 11/1981 | Norris, Jr. |
| 4,378,804 A | 4/1983 | Cortese |
| 4,560,373 A | 12/1985 | Sugino et al. |
| 4,646,480 A | 3/1987 | Williams |
| 4,646,482 A | 3/1987 | Chitjian |
| 4,655,743 A | 4/1987 | Hyde |
| 4,676,749 A | 6/1987 | Mabille |
| 4,706,676 A | 11/1987 | Peck |
| 4,718,467 A | 1/1988 | Di Gianfilippo et al. |
| 4,754,756 A | 7/1988 | Shelanski |
| 4,757,814 A | 7/1988 | Wang et al. |
| 4,764,362 A | 8/1988 | Barchas |
| 4,795,421 A | 1/1989 | Blasius, Jr. et al. |
| 4,811,734 A | 3/1989 | McGurk-Burleson et al. |
| 4,836,192 A | 6/1989 | Abbate |
| 4,875,287 A | 10/1989 | Creasy et al. |
| 4,886,078 A | 12/1989 | Shiffman |
| 4,887,994 A | 12/1989 | Bedford |
| 4,900,316 A | 2/1990 | Yamamoto |
| 4,917,086 A | 4/1990 | Feltovich et al. |
| 4,925,450 A | 5/1990 | Imonti et al. |
| 4,957,747 A | 9/1990 | Stiefel |
| 5,006,004 A | 4/1991 | Dirksing et al. |
| 5,006,339 A | 4/1991 | Bargery et al. |
| 5,012,797 A | 5/1991 | Liang et al. |
| 5,035,089 A | 7/1991 | Tillman et al. |
| 5,037,431 A | 8/1991 | Summers et al. |
| 5,037,432 A | 8/1991 | Molinari |
| 5,054,339 A | 10/1991 | Yacowitz |
| 5,100,412 A | 3/1992 | Rosso |
| 5,100,424 A | 3/1992 | Jang |
| 5,119,839 A | 6/1992 | Rudolph |
| 5,122,153 A | 6/1992 | Harrel |
| 5,171,215 A | 12/1992 | Flanagan |
| 5,192,269 A | 3/1993 | Poli et al. |
| 5,207,234 A | 5/1993 | Rosso |
| 5,222,956 A | 6/1993 | Waldron |
| 5,242,433 A | 9/1993 | Smith et al. |
| 5,254,109 A | 10/1993 | Smith et al. |
| 5,368,581 A | 11/1994 | Smith et al. |
| 5,387,215 A | 2/1995 | Fisher |
| 5,391,151 A | 2/1995 | Wilmot |
| 5,417,674 A | 5/1995 | Smith et al. |
| 5,419,772 A | 5/1995 | Teitz et al. |
| 5,441,490 A | 8/1995 | Svedman |
| 5,460,620 A | 10/1995 | Smith et al. |
| 5,470,323 A | 11/1995 | Smith et al. |
| 5,484,427 A | 1/1996 | Gibbons |
| 5,490,736 A | 2/1996 | Haber et al. |
| 5,512,044 A | 4/1996 | Duer |
| 5,562,642 A | 10/1996 | Smith et al. |
| 5,562,643 A | 10/1996 | Johnson |
| 5,611,687 A | 3/1997 | Wagner |
| 5,612,797 A | 3/1997 | Liang et al. |
| 5,674,235 A | 10/1997 | Parisi |
| 5,676,643 A | 10/1997 | Cann et al. |
| 5,676,648 A | 10/1997 | Henley |
| 5,683,971 A | 11/1997 | Rose et al. |
| 5,697,920 A | 12/1997 | Gibbons |
| 5,707,383 A | 1/1998 | Bays |
| 5,713,785 A | 2/1998 | Nishio |
| 5,735,833 A | 4/1998 | Olson |
| 5,759,185 A | 6/1998 | Grinberg |
| 5,762,640 A | 6/1998 | Kajiwara et al. |
| 5,779,519 A | 7/1998 | Oliver |
| 5,800,446 A | 9/1998 | Banuchi |
| 5,807,353 A | 9/1998 | Schmitz |
| 5,810,842 A | 9/1998 | Di Fiore |
| 5,813,416 A | 9/1998 | Rudolph |
| 5,817,050 A | 10/1998 | Klein |
| 5,846,215 A | 12/1998 | Zygmont |
| 5,848,998 A | 12/1998 | Marasco, Jr. |
| 5,857,995 A | 1/1999 | Thomas et al. |
| 5,861,142 A | 1/1999 | Schick |
| 5,873,881 A | 2/1999 | McEwen et al. |
| 5,879,323 A | 3/1999 | Henley |
| 5,882,201 A | 3/1999 | Salem |
| 5,885,260 A | 3/1999 | Mehl, Sr. et al. |
| 5,908,401 A | 6/1999 | Henley |
| 5,919,152 A | 7/1999 | Zygmont |
| 5,954,730 A | 9/1999 | Bernabei |
| 5,971,999 A | 10/1999 | Naldoni |
| 5,980,555 A | 11/1999 | Barbut et al. |
| 6,019,749 A | 2/2000 | Fields et al. |
| 6,023,639 A | 2/2000 | Hakky et al. |
| 6,024,733 A | 2/2000 | Eggers et al. |
| 6,027,402 A | 2/2000 | Oliver |
| 6,039,745 A | 3/2000 | Di Fiore et al. |
| 6,042,552 A | 3/2000 | Cornier |
| 6,080,165 A | 6/2000 | DeJacma |
| 6,080,166 A | 6/2000 | McEwen et al. |
| 6,090,085 A | 7/2000 | Mehl, Sr. et al. |
| 6,120,512 A | 9/2000 | Bernabei |
| 6,129,701 A | 10/2000 | Cimino |
| 6,136,008 A | 10/2000 | Becker et al. |
| 6,139,553 A | 10/2000 | Dotan |
| 6,139,554 A | 10/2000 | Karkar et al. |
| 6,142,155 A | 11/2000 | Rudolph |
| 6,149,634 A | 11/2000 | Bernabei |
| 6,159,226 A | 12/2000 | Kim |
| 6,162,218 A | 12/2000 | Elbrecht et al. |
| 6,162,232 A | 12/2000 | Shadduck |
| 6,165,059 A | 12/2000 | Park et al. |
| 6,183,451 B1 | 2/2001 | Mehl, Sr. et al. |
| 6,183,483 B1 | 2/2001 | Chang |

(56) References Cited

U.S. PATENT DOCUMENTS

| | | |
|---|---|---|
| 6,193,589 B1 | 2/2001 | Khalaj |
| 6,196,982 B1 | 3/2001 | Ball |
| 6,231,593 B1 | 5/2001 | Meserol |
| 6,235,039 B1 | 5/2001 | Parkin et al. |
| 6,238,275 B1 | 5/2001 | Metcalf et al. |
| 6,241,739 B1 | 6/2001 | Waldron |
| 6,264,666 B1 | 7/2001 | Coleman et al. |
| 6,277,128 B1 | 8/2001 | Muldner |
| 6,283,978 B1 | 9/2001 | Cheski et al. |
| 6,299,620 B1 | 10/2001 | Shadduck |
| 6,306,119 B1 | 10/2001 | Weber et al. |
| 6,306,147 B1 | 10/2001 | Bernabei et al. |
| 6,322,548 B1 | 11/2001 | Payne et al. |
| 6,322,568 B1 | 11/2001 | Bernabei et al. |
| 6,332,886 B1 | 12/2001 | Green et al. |
| 6,368,333 B2 | 4/2002 | Bernabei et al. |
| 6,387,103 B2 | 5/2002 | Shadduck |
| 6,401,289 B1 | 6/2002 | Herbert |
| 6,409,736 B1 | 6/2002 | Bernabei |
| 6,410,599 B1 | 6/2002 | Johnson |
| RE37,796 E | 7/2002 | Henley |
| 6,414,032 B1 | 7/2002 | Johnson |
| 6,420,431 B1 | 7/2002 | Johnson |
| 6,423,078 B1 | 7/2002 | Bays et al. |
| 6,423,750 B1 | 7/2002 | Johnson |
| 6,432,113 B1 | 8/2002 | Parkin et al. |
| 6,432,114 B1 | 8/2002 | Rosso |
| 6,471,712 B2 | 10/2002 | Burres |
| 6,477,410 B1 | 11/2002 | Henley et al. |
| 6,482,212 B1 | 11/2002 | Bernabei et al. |
| 6,488,646 B1 | 12/2002 | Zygmont |
| 6,494,856 B1 | 12/2002 | Zygmont |
| 6,500,183 B1 | 12/2002 | Waldron |
| 6,503,256 B2 | 1/2003 | Parkin et al. |
| 6,511,486 B2 | 1/2003 | Mercier et al. |
| 6,514,262 B1 | 2/2003 | Di Fiore et al. |
| 6,527,783 B1 | 3/2003 | Ignon |
| 6,535,761 B2 | 3/2003 | Bernabei |
| 6,540,757 B1 | 4/2003 | Hruska et al. |
| 6,562,013 B1 | 5/2003 | Marasco, Jr. |
| 6,562,050 B1 | 5/2003 | Owen |
| 6,564,093 B1 | 5/2003 | Ostrow et al. |
| 6,565,535 B2 | 5/2003 | Zaias et al. |
| 6,582,442 B2 | 6/2003 | Simon et al. |
| 6,589,218 B2 | 7/2003 | Garcia |
| 6,592,595 B1 | 7/2003 | Mallett et al. |
| 6,629,983 B1 | 10/2003 | Ignon |
| 6,641,591 B1 | 11/2003 | Shadduck |
| 6,645,184 B1 | 11/2003 | Zelickson et al. |
| 6,652,888 B2 | 11/2003 | Rhoades |
| 6,666,874 B2 | 12/2003 | Heitzmann et al. |
| 6,673,081 B1 | 1/2004 | Tavger et al. |
| 6,673,082 B2 | 1/2004 | Mallett et al. |
| 6,685,853 B1 | 2/2004 | Angelopoulous et al. |
| 6,687,537 B2 | 2/2004 | Bernabei |
| 6,695,853 B2 | 2/2004 | Karasiuk |
| 6,735,470 B2 | 5/2004 | Henley et al. |
| 6,743,211 B1 * | 6/2004 | Prausnitz et al. ............ 604/239 |
| 6,743,215 B2 | 6/2004 | Bernabei |
| 6,764,493 B1 | 7/2004 | Weber et al. |
| 6,800,083 B2 | 10/2004 | Hiblar et al. |
| 6,869,611 B1 | 3/2005 | Kligman et al. |
| 6,905,487 B2 | 6/2005 | Zimmerman |
| 6,911,031 B2 | 6/2005 | Muldner |
| 6,924,649 B2 | 8/2005 | Knoedgen |
| 6,926,681 B1 | 8/2005 | Ramey et al. |
| 6,942,649 B2 | 9/2005 | Ignon et al. |
| 6,960,206 B2 | 11/2005 | Keane |
| 7,001,355 B2 | 2/2006 | Nunomura et al. |
| 7,004,933 B2 | 2/2006 | McDaniel |
| 7,044,938 B2 | 5/2006 | La Bianco et al. |
| 7,052,503 B2 | 5/2006 | Bernabei |
| 7,069,073 B2 | 6/2006 | Henley et al. |
| 7,070,488 B2 | 7/2006 | Suissa et al. |
| 7,083,580 B2 | 8/2006 | Bernabei |
| 7,087,063 B2 | 8/2006 | Carson et al. |
| 7,094,252 B2 | 8/2006 | Koop |
| 7,115,275 B2 | 10/2006 | Clarot et al. |
| 7,135,011 B2 | 11/2006 | Powers et al. |
| 7,153,311 B2 | 12/2006 | Chung |
| 7,197,359 B1 | 3/2007 | Tokudome et al. |
| 7,198,623 B2 | 4/2007 | Fischer et al. |
| 7,232,444 B2 | 6/2007 | Chang |
| 7,241,208 B2 | 7/2007 | Suissa et al. |
| 7,276,051 B1 | 10/2007 | Henley et al. |
| 7,293,930 B2 | 11/2007 | Chuang |
| 7,314,326 B2 | 1/2008 | Rosenberg |
| 7,316,657 B2 | 1/2008 | Kleinhenz et al. |
| 7,318,828 B1 | 1/2008 | Revivo |
| 7,320,691 B2 | 1/2008 | Pilcher et al. |
| 7,320,801 B2 | 1/2008 | Kelly |
| 7,354,423 B2 | 4/2008 | Zelickson et al. |
| 7,364,565 B2 | 4/2008 | Freeman |
| 7,384,405 B2 | 6/2008 | Rhoades |
| 7,427,273 B2 | 9/2008 | Mitsui |
| 7,458,944 B2 | 12/2008 | Liste et al. |
| 7,476,205 B2 | 1/2009 | Erdmann |
| 7,477,938 B2 | 1/2009 | Sun et al. |
| 7,482,314 B2 | 1/2009 | Grimes et al. |
| 7,485,125 B2 | 2/2009 | Sjostrom |
| 7,489,989 B2 | 2/2009 | Sukhanov et al. |
| 7,507,228 B2 | 3/2009 | Sun et al. |
| 7,582,067 B2 | 9/2009 | Van Acker |
| 7,597,900 B2 | 10/2009 | Zimmer et al. |
| 7,597,901 B2 | 10/2009 | Clarot et al. |
| 7,658,742 B2 | 2/2010 | Karasiuk |
| 7,678,120 B2 | 3/2010 | Shadduck |
| 7,744,582 B2 | 6/2010 | Sadowski et al. |
| 7,789,886 B2 | 9/2010 | Shadduck |
| 7,837,695 B2 | 11/2010 | Hart et al. |
| 7,901,373 B2 | 3/2011 | Tavger |
| 7,951,156 B2 | 5/2011 | Karasiuk |
| 7,993,333 B2 | 8/2011 | Oral et al. |
| 8,025,669 B1 | 9/2011 | David et al. |
| RE42,960 E | 11/2011 | Waldron |
| 8,048,089 B2 | 11/2011 | Ignon et al. |
| 8,066,716 B2 | 11/2011 | Shadduck |
| 8,088,085 B2 | 1/2012 | Thiebaut et al. |
| 8,105,295 B2 | 1/2012 | Blott et al. |
| 8,128,638 B2 | 3/2012 | Karasiuk et al. |
| 8,221,437 B2 | 7/2012 | Waldron et al. |
| 8,236,008 B2 | 8/2012 | Boone, III et al. |
| 8,277,287 B2 | 10/2012 | Hart |
| 8,337,513 B2 | 12/2012 | Shadduck |
| 8,343,116 B2 | 1/2013 | Ignon et al. |
| 8,814,836 B2 | 8/2014 | Ignon et al. |
| 9,056,193 B2 | 6/2015 | Ignon et al. |
| 9,468,464 B2 | 10/2016 | Shadduck |
| 9,474,886 B2 | 10/2016 | Ignon et al. |
| 9,486,615 B2 | 11/2016 | Ignon et al. |
| 9,498,610 B2 | 11/2016 | Ignon et al. |
| 9,550,052 B2 | 1/2017 | Ignon et al. |
| 9,566,088 B2 | 2/2017 | Ignon et al. |
| 9,642,997 B2 | 5/2017 | Ignon et al. |
| 9,662,482 B2 | 5/2017 | Ignon et al. |
| 9,775,646 B2 | 10/2017 | Shadduck |
| 9,814,868 B2 | 11/2017 | Ignon et al. |
| 10,035,007 B2 | 7/2018 | Ignon et al. |
| 2001/0023351 A1 | 9/2001 | Eilers |
| 2001/0037118 A1 | 11/2001 | Shadduck |
| 2001/0049511 A1 | 12/2001 | Coleman et al. |
| 2002/0016601 A1 | 2/2002 | Shadduck |
| 2002/0041891 A1 | 4/2002 | Cheski |
| 2002/0058952 A1 | 5/2002 | Weber et al. |
| 2002/0107527 A1 | 8/2002 | Burres |
| 2002/0128663 A1 | 9/2002 | Mercier et al. |
| 2002/0133110 A1 | 9/2002 | Citow |
| 2002/0133176 A1 | 9/2002 | Parkin et al. |
| 2002/0151826 A1 | 10/2002 | Ramey et al. |
| 2002/0151908 A1 | 10/2002 | Mallett, Sr. |
| 2002/0188261 A1 | 12/2002 | Hruska |
| 2003/0012415 A1 | 1/2003 | Cossel |
| 2003/0018252 A1 | 1/2003 | Duchon et al. |
| 2003/0060834 A1 | 3/2003 | Muldner |

(56) References Cited

U.S. PATENT DOCUMENTS

| | | |
|---|---|---|
| 2003/0093040 A1 | 5/2003 | Mikszta et al. |
| 2003/0093089 A1 | 5/2003 | Greenberg |
| 2003/0097139 A1 | 5/2003 | Karasiuk |
| 2003/0167032 A1* | 9/2003 | Ignon .............................. 604/19 |
| 2003/0187462 A1 | 10/2003 | Chang |
| 2003/0208159 A1 | 11/2003 | Ignon et al. |
| 2003/0212127 A1 | 11/2003 | Glassman et al. |
| 2003/0212415 A1 | 11/2003 | Karasiuk |
| 2004/0010222 A1 | 1/2004 | Nunomura et al. |
| 2004/0010269 A1 | 1/2004 | Grimes et al. |
| 2004/0015139 A1 | 1/2004 | La Bianco |
| 2004/0087972 A1 | 5/2004 | Mulholland et al. |
| 2004/0092895 A1 | 5/2004 | Harmon |
| 2004/0092959 A1 | 5/2004 | Bernaz |
| 2004/0097967 A1 | 5/2004 | Ignon |
| 2004/0122447 A1 | 6/2004 | Harmon et al. |
| 2004/0127914 A1 | 7/2004 | Chung |
| 2004/0143274 A1 | 7/2004 | Shadduck |
| 2004/0162565 A1 | 8/2004 | Carson et al. |
| 2004/0166172 A1 | 8/2004 | Rosati et al. |
| 2004/0219179 A1 | 11/2004 | McDaniel |
| 2004/0236291 A1 | 11/2004 | Zelickson et al. |
| 2004/0243149 A1 | 12/2004 | Lee, Jr. |
| 2004/0254587 A1 | 12/2004 | Park |
| 2004/0267285 A1 | 12/2004 | Chang |
| 2005/0037034 A1 | 2/2005 | Rhoades |
| 2005/0038448 A1 | 2/2005 | Chung |
| 2005/0059940 A1 | 3/2005 | Weber et al. |
| 2005/0084509 A1 | 4/2005 | Bernstein |
| 2005/0148958 A1 | 7/2005 | Rucinski |
| 2005/0203111 A1 | 9/2005 | David |
| 2005/0209611 A1 | 9/2005 | Greenberg |
| 2005/0283176 A1 | 12/2005 | Law |
| 2006/0002960 A1 | 1/2006 | Zoeteweij et al. |
| 2006/0116674 A1 | 6/2006 | Goble et al. |
| 2006/0161178 A1 | 7/2006 | Lee |
| 2006/0189964 A1 | 8/2006 | Anderson |
| 2006/0191562 A1 | 8/2006 | Numomura |
| 2006/0200099 A1 | 9/2006 | La Bianco et al. |
| 2006/0200172 A1 | 9/2006 | Shadduck |
| 2006/0200173 A1 | 9/2006 | Shadduck |
| 2006/0212029 A1 | 9/2006 | Arcusa Villacampa et al. |
| 2006/0253125 A1 | 11/2006 | Ignon |
| 2006/0264893 A1 | 11/2006 | Sage, Jr. et al. |
| 2007/0005078 A1 | 1/2007 | Hart et al. |
| 2007/0043382 A1 | 2/2007 | Cheney |
| 2007/0065515 A1 | 3/2007 | Key |
| 2007/0088371 A1 | 4/2007 | Karasiuk |
| 2007/0123808 A1 | 5/2007 | Rhoades |
| 2007/0154502 A1 | 7/2007 | Hattendorf et al. |
| 2007/0156124 A1 | 7/2007 | Ignon et al. |
| 2007/0178121 A1 | 8/2007 | First et al. |
| 2007/0198031 A1 | 8/2007 | Kellogg |
| 2007/0208353 A1 | 9/2007 | Shadduck |
| 2007/0239173 A1 | 10/2007 | Khalaj |
| 2008/0027328 A1 | 1/2008 | Klopotek et al. |
| 2008/0091179 A1 | 4/2008 | Durkin et al. |
| 2008/0103563 A1 | 5/2008 | Powell |
| 2008/0119781 A1 | 5/2008 | King |
| 2008/0132914 A1 | 6/2008 | Bossard et al. |
| 2008/0139974 A1 | 6/2008 | Da Silva |
| 2008/0154161 A1 | 6/2008 | Abbott |
| 2008/0193493 A1 | 8/2008 | Rhoades |
| 2008/0200861 A1 | 8/2008 | Shalev et al. |
| 2008/0208146 A1* | 8/2008 | Brandwein ........ A61M 37/0015 604/272 |
| 2008/0214987 A1 | 9/2008 | Xu |
| 2008/0215068 A1 | 9/2008 | Hart et al. |
| 2008/0221548 A1* | 9/2008 | Danenberg et al. .......... 604/506 |
| 2008/0243039 A1 | 10/2008 | Rhoades |
| 2008/0287864 A1 | 11/2008 | Rosenberg |
| 2008/0300529 A1 | 12/2008 | Reinstein |
| 2008/0300552 A1 | 12/2008 | Cichocki et al. |
| 2009/0048557 A1 | 2/2009 | Yeshurun et al. |
| 2009/0053390 A1 | 2/2009 | Sakou et al. |
| 2009/0062815 A1 | 3/2009 | Karasiuk et al. |
| 2009/0099091 A1 | 4/2009 | Hantash |
| 2009/0099093 A1 | 4/2009 | Hantash |
| 2009/0124985 A1 | 5/2009 | Hasenoehrl et al. |
| 2009/0138026 A1 | 5/2009 | Wu |
| 2009/0177171 A1 | 7/2009 | Ignon et al. |
| 2009/0192442 A1* | 7/2009 | Ignon et al. ..................... 604/22 |
| 2009/0222023 A1 | 9/2009 | Boone, III et al. |
| 2010/0045427 A1 | 2/2010 | Boone, III et al. |
| 2010/0049177 A1 | 2/2010 | Boone, III et al. |
| 2010/0049210 A1 | 2/2010 | Boone, III et al. |
| 2010/0217357 A1 | 8/2010 | Da Silva |
| 2010/0305495 A1 | 12/2010 | Anderson et al. |
| 2011/0054490 A1 | 3/2011 | Hart |
| 2011/0066162 A1 | 3/2011 | Cohen |
| 2011/0082415 A1 | 4/2011 | Ignon et al. |
| 2012/0022435 A1 | 1/2012 | Ignon et al. |
| 2012/0041338 A1* | 2/2012 | Chickering et al. .......... 600/575 |
| 2012/0136374 A1 | 5/2012 | Karasiuk |
| 2013/0004230 A1 | 1/2013 | Kirk, III et al. |
| 2013/0018317 A1 | 1/2013 | Bobroff et al. |
| 2013/0066336 A1 | 3/2013 | Boone, III et al. |
| 2013/0096577 A1 | 4/2013 | Shadduck |
| 2013/0102978 A1 | 4/2013 | Ignon et al. |
| 2013/0144280 A1 | 6/2013 | Eckhouse et al. |
| 2013/0158547 A1 | 6/2013 | David |
| 2014/0343481 A1 | 11/2014 | Ignon |
| 2014/0343574 A1 | 11/2014 | Ignon et al. |
| 2015/0032047 A1 | 1/2015 | Ignon et al. |
| 2015/0230824 A1 | 8/2015 | Shadduck |
| 2015/0230825 A1 | 8/2015 | Shadduck |
| 2015/0231379 A1 | 8/2015 | Ignon et al. |
| 2015/0265822 A1 | 9/2015 | Ignon et al. |
| 2015/0272623 A1 | 10/2015 | Ignon et al. |
| 2015/0290442 A1 | 10/2015 | Ignon et al. |
| 2016/0038183 A1 | 2/2016 | Ignon et al. |
| 2016/0256671 A1 | 9/2016 | Ignon et al. |
| 2017/0036002 A1 | 2/2017 | Ignon et al. |
| 2017/0065801 A1 | 3/2017 | Ignon et al. |
| 2017/0209894 A1 | 7/2017 | Sporrer |
| 2017/0224972 A1 | 8/2017 | Ignon et al. |
| 2017/0245876 A1 | 8/2017 | Ignon et al. |
| 2017/0266424 A1 | 9/2017 | Ignon et al. |
| 2017/0319835 A1 | 11/2017 | Ignon et al. |
| 2017/0319836 A1 | 11/2017 | Ignon et al. |
| 2017/0333689 A1 | 11/2017 | Ignon et al. |

FOREIGN PATENT DOCUMENTS

| | | |
|---|---|---|
| CA | 2 340 154 | 9/2002 |
| DE | 59 95 21 | 7/1934 |
| DE | 24 15 633 | 10/1975 |
| DE | 33 38 057 | 8/1984 |
| DE | 34 21 390 A1 | 12/1985 |
| DE | 234 608 | 4/1986 |
| DE | 35 03 343 | 8/1986 |
| DE | 83 30 191 | 6/1987 |
| DE | 37 40 902 | 12/1988 |
| DE | 42 37 940 | 5/1993 |
| DE | 298 08 395 | 8/1998 |
| DE | 10 2004 015815 A1 | 11/2005 |
| EP | 0 258 901 | 9/1987 |
| EP | 0 564 392 | 3/1993 |
| EP | 0 784 997 | 7/1997 |
| EP | 2106780 | 3/2016 |
| ES | 1 037 776 | 4/1998 |
| FR | 2 712 172 | 5/1995 |
| FR | 2 773 461 | 7/1999 |
| GB | 1 372 609 | 10/1974 |
| GB | 2306351 | 5/1997 |
| IT | 553 076 | 12/1956 |
| IT | 118 49 22 | 3/1985 |
| JP | H05-042060 | 2/1993 |
| JP | 1993-088552 | 12/1993 |
| JP | 09-294747 | 11/1997 |
| JP | 2003-534881 | 11/2003 |
| JP | 2003-339713 | 12/2003 |
| JP | 2004-275721 | 10/2004 |
| JP | 2006-503627 | 2/2006 |

(56) References Cited

FOREIGN PATENT DOCUMENTS

| | | |
|---|---|---|
| JP | 2006-204767 | 10/2006 |
| KR | 20-0280320 | 7/2002 |
| KR | 10-2007007017 | 7/2007 |
| WO | WO 1994/024980 | 11/1994 |
| WO | WO 1997/011650 | 3/1997 |
| WO | WO 2000/015300 | 3/2000 |
| WO | WO 2001/93931 | 12/2001 |
| WO | WO 2003/073917 | 9/2003 |
| WO | WO 2004/037098 | 5/2004 |
| WO | WO 2005/070313 | 8/2005 |
| WO | WO 2006/018731 | 2/2006 |
| WO | WO 2006/031413 | 3/2006 |
| WO | WO 2007/114904 | 10/2007 |
| WO | WO 2009/088884 | 7/2009 |
| WO | WO 2009/097451 | 8/2009 |
| WO | WO 2012/145667 | 10/2012 |

OTHER PUBLICATIONS

Cox III et al., *Decreased Splatter in Dermabrasion*, Arch Facial Plastic Surgery, Jan.-Mar. 2000, vol. 2, pp. 23-26.

Ditre et al., *Effect of α-hydroxy acids on photoaged skin: A pilot clinical, histologic, and ultrastructural study*, Journal of American Academy of Dermatology, Feb. 1996, vol. 34, No. 2, Part 1, pp. 187-195.

Harris et al., *Combining Manual Dermasanding with Low Stregnth Trichloroacetic Acid to Improve Antinically Injured Skin*, The Journal of Dermatologic Surgery and Oncology, Jul. 1994, vol. 20, No. 7, pp. 436-442.

Microdermabrader Pepita Instruction Manual, Mattioli Engineering S.R.L., PEP_USA2.doc Rev 1.1, Sep. 29, 1997.

\* cited by examiner

SKIN TREATMENT SYSTEMS AND METHODS USING NEEDLES

CROSS-REFERENCE TO RELATED APPLICATIONS

This application claims the priority benefit under 35 U.S.C. § 119(e) of U.S. Provisional Application No. 61/788,420, filed Mar. 15, 2013, the entirety of which is hereby incorporated by reference herein.

BACKGROUND

Field

This application relates generally to skin treatment, and more specifically, to apparatuses, systems and methods for treating a person's skin using one or more needles and/or other penetrating members.

Description of the Related Art

Abrasion of the outer layer or epidermis of the skin is desirable to smooth or blend scars, blemishes or other skin conditions that may be caused by, for example, sun exposure, acne, other skin disorders, aging and/or the like. Standard techniques used to abrade the skin have generally been separated into two fields referred to as dermabrasion and microdermabrasion. In both techniques, portions of the epidermis called the stratum corneum are removed. The body then replaces the lost skin cells, resulting in a new outer layer of skin. Additionally, despite the mild edema and erythema associated with the procedures, the skin looks and feels smoother because of the new outer layer of skin.

SUMMARY

According to some embodiments disclosed in the present application, a device for treating the skin comprises a handpiece assembly having a distal end and a proximal end. The handpiece assembly further comprises a main body portion and a tip on the distal end of the main body portion. In some embodiments, the handpiece assembly includes one or more fluid delivery conduits, one or more waste conduits and/or one or more energy conduits. In some embodiments, the handpiece assembly comprises a cartridge comprising an inner cavity. In addition, the cartridge is coupled to the handpiece assembly with the inner cavity of the cartridge being in fluid communication with the fluid delivery conduit. In some embodiments, the main body portion comprises an interior volume in which one or more of the conduits can be located. Further, the tip is configured to contact the skin.

In some embodiments, the tip is configured to be removable from the main body portion. In some embodiments, the main body portion and tip are a single unitary piece. The tip comprises a plurality of needles, a base member, and a peripheral lip, ridge, outer peripheral member or the like and. The tip can also comprise one or more openings in fluid communication with a waste conduit, one or more openings in communication with a fluid delivery conduit and/or one or more energy contact points in electrical communication with an energy source. In some embodiments the tip comprises one or more hollow needles, the hollow needles in fluid communication with a fluid delivery conduit. In some embodiments, one or more of the needles in the tip is in electrical communication with an energy conduit. In some embodiments, the handpiece assembly includes a source of pressure (e.g. pneumatic pressure) configured to move the plurality of needles and/or the base member with respect to the peripheral lip of the tip.

According to some embodiments disclosed in the present application, a method of treating the skin includes providing a handpiece assembly comprising a body and a tip having a distal end. The handpiece assembly includes a waste conduit and a fluid delivery conduit that are in fluid communication with the distal end of the tip. The tip comprises a peripheral lip and a plurality of needles. The method further includes placing the delivery conduit of the handpiece assembly in fluid communication with a fluid source for delivering at least one treatment fluid to the distal end of the tip and placing the waste conduit of the handpiece assembly in fluid communication with a suction source for removing waste materials from the distal end of the tip. In addition, the method comprises placing the peripheral lip the tip in contact with a person's skin. The method further comprises activating the suction source and causing the plurality of needles to penetrate the person's skin. The method also comprises delivering a treatment fluid to the distal end of the tip. In some embodiments, the treatment fluid comprises human growth factors, cytokines, soluble collagen, antioxidants, matrix proteins, serums, water, saline and/or any other fluids or materials, either alone or in combination.

According to other embodiments disclosed in the present application, a method of treating the skin comprises providing a handpiece assembly comprising a body and a tip having a distal end. The tip comprises a peripheral lip and a plurality of hollow needles. The handpiece assembly includes a waste conduit in fluid communication with the distal end of the tip and a delivery conduit in communication with the plurality of hollow needles. In addition, the method comprises placing the peripheral lip of the tip in contact with a person's skin. The method further comprises activating the suction source and causing the plurality of needles to penetrate the person's skin. The method also comprises delivering a treatment fluid to the plurality of hollow needles. In some embodiments, the treatment fluid comprises human growth factors, cytokines, soluble collagen, antioxidants, matrix proteins, serums, water, saline, dermal fillers, hot or cold vapors and/or gases and/or any other fluids or materials, either alone or in combination.

According to other embodiments disclosed in the present application, a method of treating the skin comprises providing a handpiece assembly comprising a body and a tip having a distal end. The tip comprises a peripheral lip and a plurality of needles. The handpiece assembly includes a waste conduit in fluid communication with the distal end of the tip and an energy conduit in communication with the plurality of needles. In addition, the method comprises placing the peripheral lip the tip in contact with a person's skin. The method further comprises activating the suction source and causing the plurality of needles to penetrate the person's skin. The method also comprises delivering energy to the plurality of needles, thus causing damage to the skin. In some embodiments, the energy source comprises radio frequency (e.g. RF energy), ultrasound, and/or microwave energy.

According to the embodiments disclosed in the present application, a method of treating the skin can further include using pneumatic or other appropriate force to move the plurality of needles and/or the base member with respect to the peripheral lip of the tip. The plurality of needles and/or the base member can be moved in this manner to a predetermined depth in the patient's skin. According to the embodiments disclosed in the present application, the methods of using needles to treat the skin as described above can be utilized in conjunction with other microdermabrasion treatments. The use of needles could occur before, during, after or in lieu of other microdermabrasion treatments.

DETAILED DESCRIPTION

Figure 1:
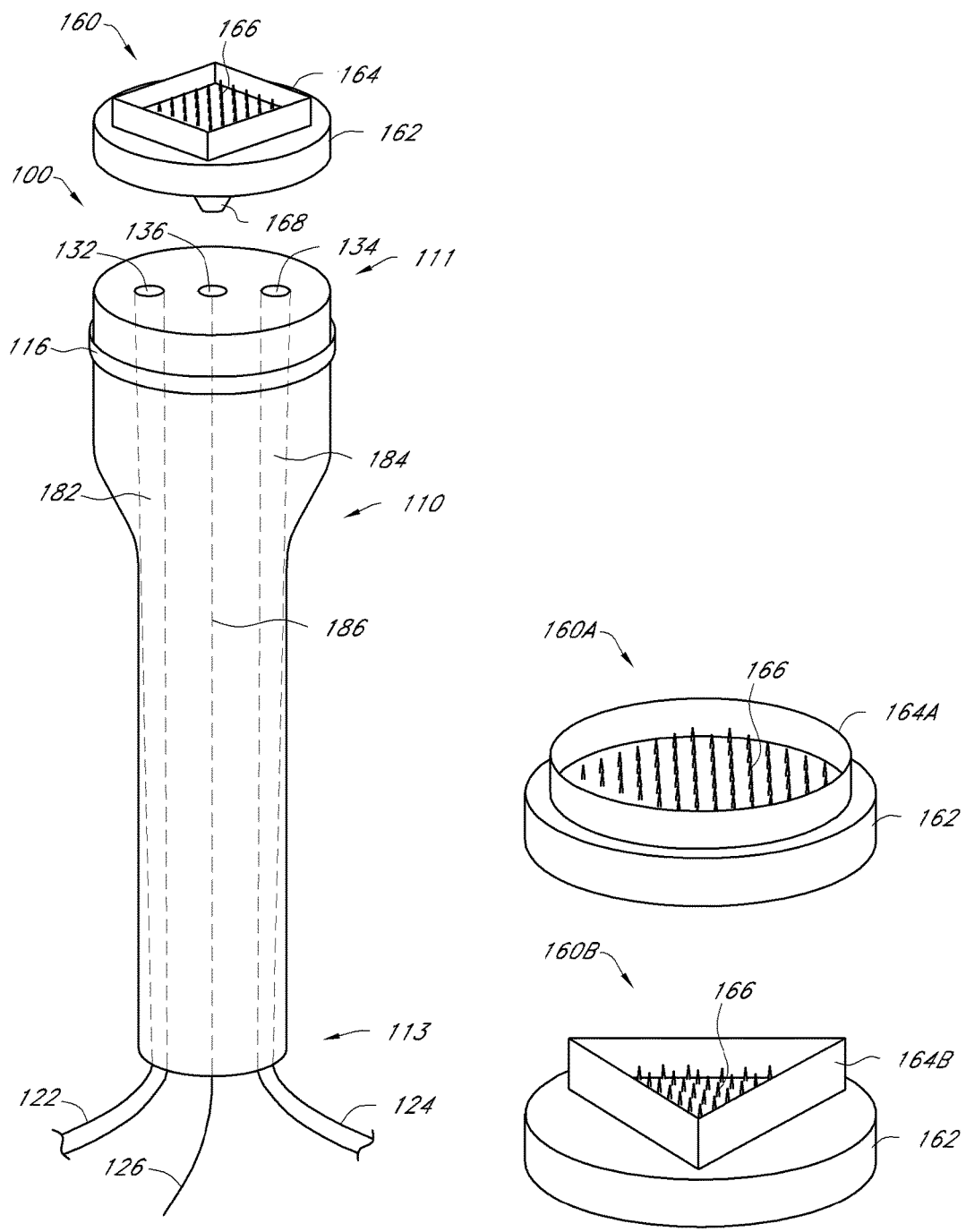
FIG. 1 is a perspective view of an embodiment of the main body portion and tip assembly, as well as additional embodiments of the tip.

FIG. 1 illustrates an embodiment of a handpiece assembly 100 for treating the skin. As shown, the assembly 100 generally comprises a main body portion 110 with a distal end 111 and a proximal end 113. The assembly 100 comprises a tip 160 configured to engage with the distal end 111 of the main body portion 110. The tip 160 can be removable from the main body portion 110. The tip 160 and main body portion 110 can also be manufactured as a unitary construction. The distal end 111 of the main body portion 110 can include one or more O-rings 116 or other sealing members. The O-rings 116 can engage with the tip skirt portion 162 so as to create a seal between the tip 160 and the main body portion 110. The main body portion can include one or more fluid delivery openings 134 in or along the distal end of the main body portion, as well as one or more suction openings 132 and energy contact points 136. A fluid delivery opening 134 can connect to a fluid source 124 via a fluid delivery conduit 184 in the main body portion 110, a suction opening 132 can connect to a suction source 122 via a suction conduit 182 in the main body portion 110, and an energy contact point 136 can connect to an energy source 126 via an energy conduit 186 in main body portion 110.

In some embodiments, the tip 160 comprises a tip skirt portion 162, a base member 165, a peripheral lip 164, a plurality of needles 166 and one or more tip ports 168. The needles within the plurality of needles 166 can be of uniform length and diameter or may vary in length (e.g. 0.5-2.5 mm) and/or diameter. The needles can comprise surgical steel (e.g., stainless steel), plastic and/or any other material suitable for penetrating the skin. The one or more tip ports 168 can engage with the fluid delivery openings 134, suction openings 132 and/or the contact points 136 along or near the distal end 111 of the main body portion 110. The peripheral lip 164 can have many shapes, as shown in the embodiments 160A, 160B of the tip 160 in FIG. 1. The tip 160 can have a rectangular peripheral lip 164, a rounded or oval peripheral lip 164A, a triangular peripheral lip 164B or any other shaped lip.

Figure 2:
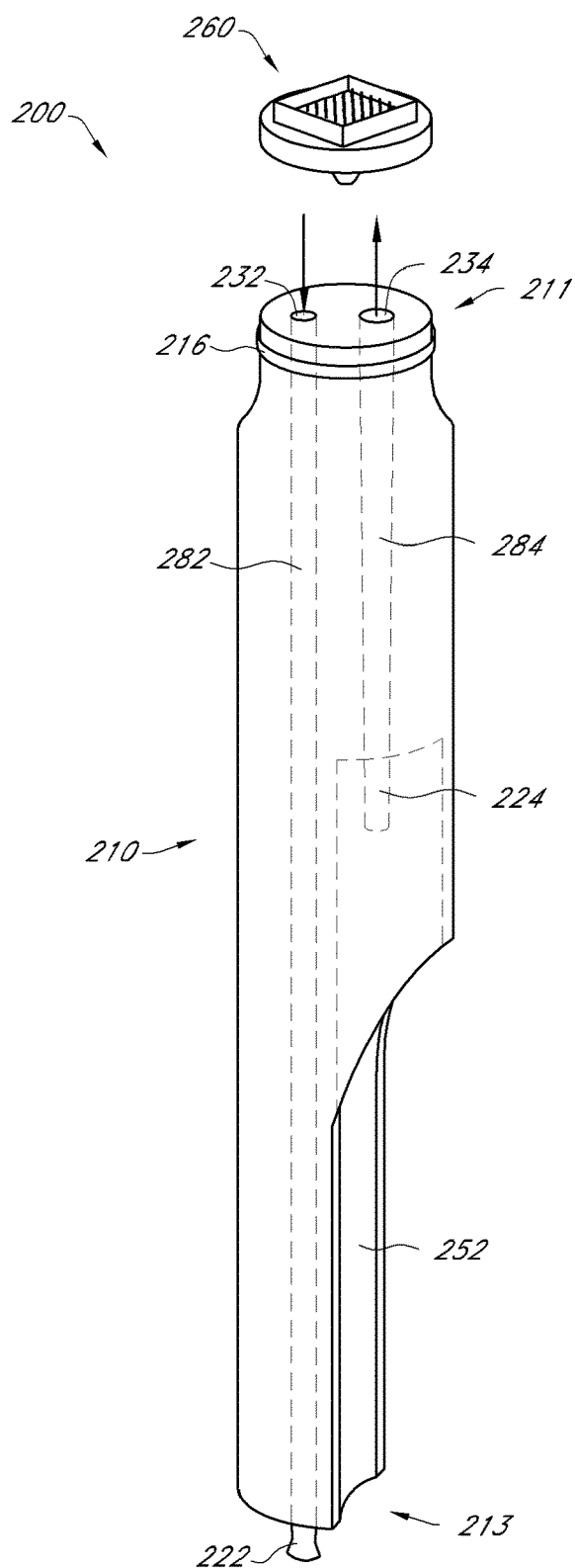
FIG. 2 is a perspective view of an embodiment of the main body portion and tip assembly showing a fluid delivery conduit positioned within a recess in the main body portion.

FIG. 2 shows an embodiment of a handpiece assembly 200 for treating the skin where the handpiece assembly 200 generally comprises a main body portion 210 and a tip 260. A fluid source point 224 can be located within a hollowed out portion 252 of the main body portion 210 and is connected to a fluid delivery opening 234 via a fluid delivery conduit 284. This embodiment could allow for the use of a fluid cartridge as a fluid source. For example, the fluid cartridge could fit into the hollowed-out portion 252 of the main body portion 210 and could engage with the fluid source point 224. The main body portion 210 could also comprise one or more O-rings 216 or other sealing members that can engage with the tip 260 to provide a seal between the tip 260 and the main body portion 210. The tip 260 can be removable from the main body portion 210. Alternatively, the main body portion 210 and tip 260 can be manufactured as a single unitary part.

Figure 3:
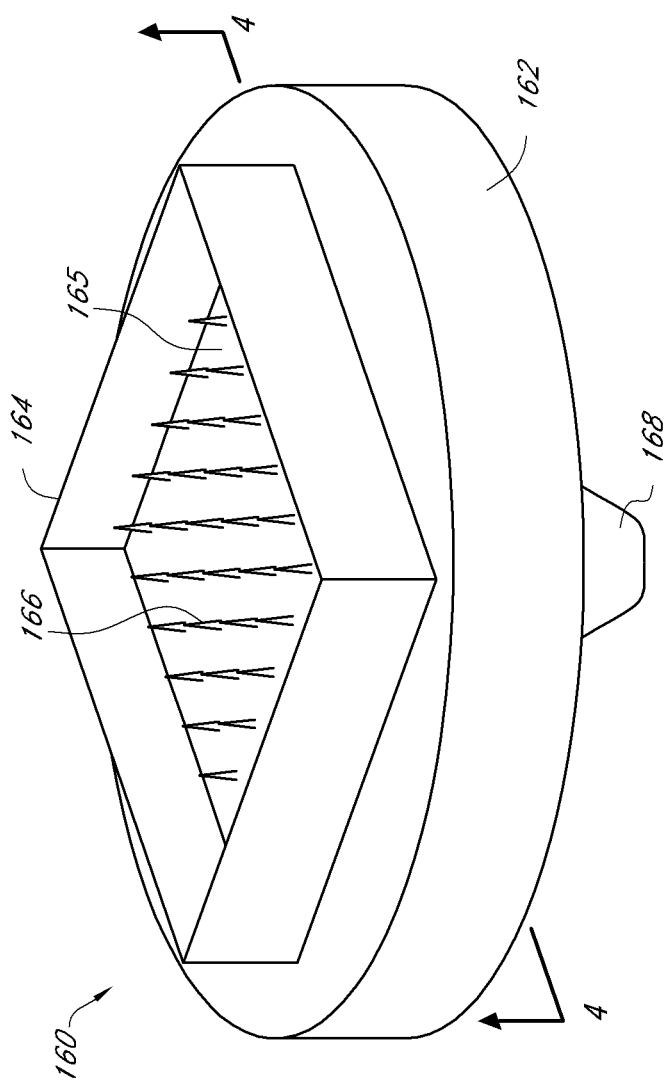
FIG. 3 is a close-up perspective view of an embodiment of the tip.
Figure 4:
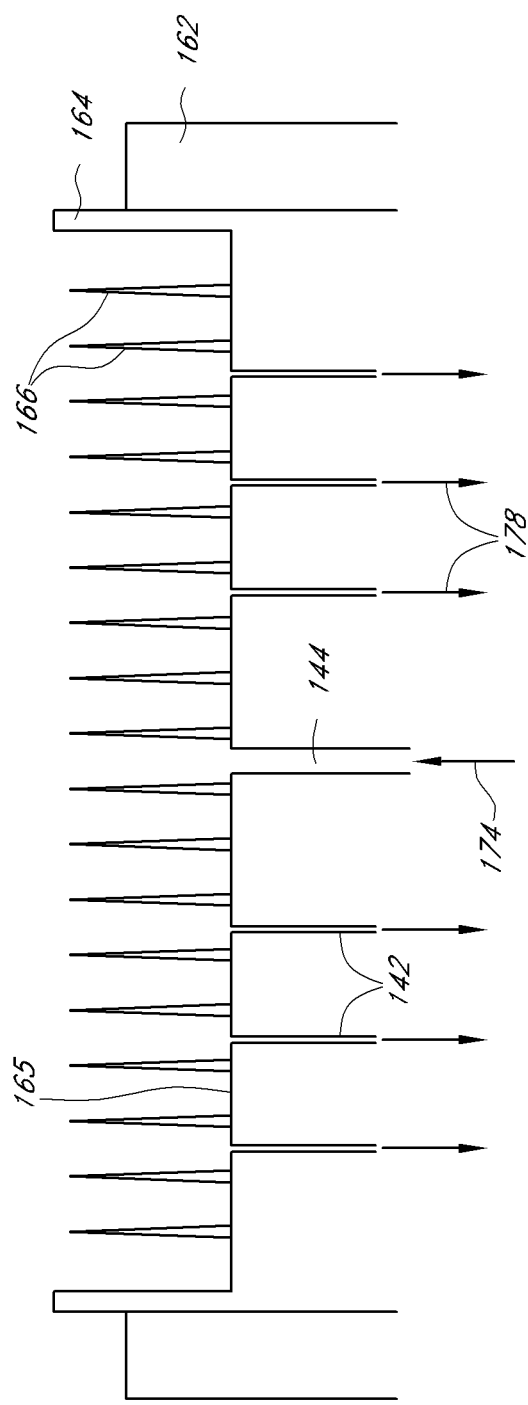
FIG. 4 is a cross-section view of an embodiment of the tip along cutting plane A-A of FIG. 3 showing a tip having multiple openings in fluid communication with a suction conduit.
Figure 4A:
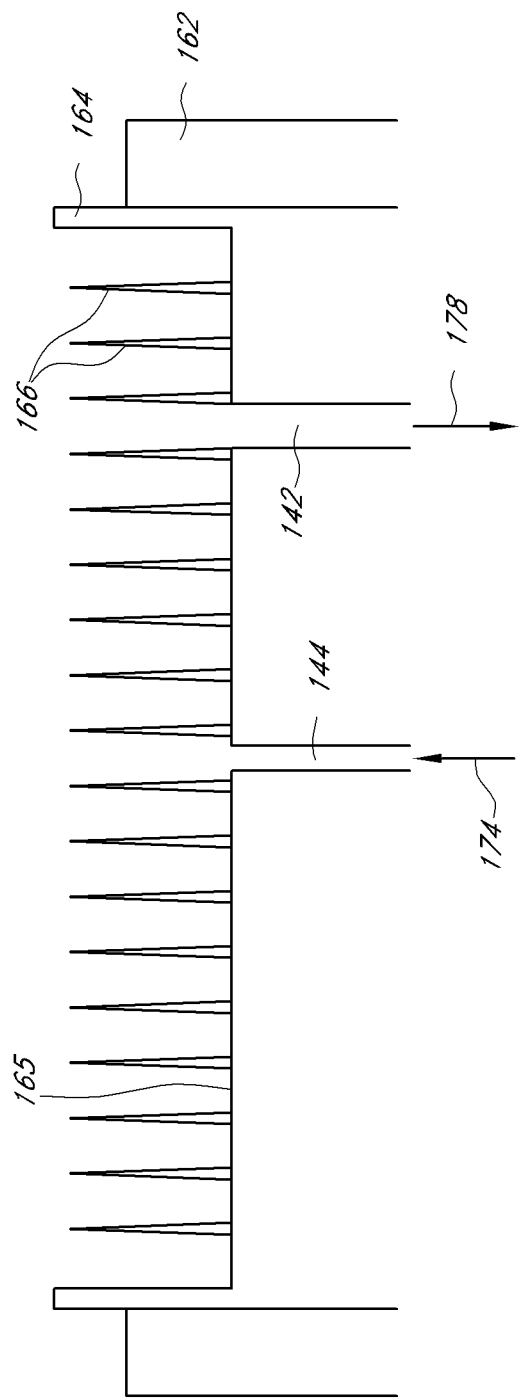
FIG. 4A is a cross-section view of an embodiment of the tip along cutting plane A-A of FIG. 3 showing tip having one opening in fluid communication with a suction conduit.

As shown in FIG. 3, a tip 160 can comprise a peripheral lip 164, a plurality of needles 166, a base member 165 and one or more tip ports 168. In some embodiments, the tip additionally comprises a tip skirt portion 162. In one embodiment, the tip skirt portion 162, the base member 165 and the peripheral lip 164 can be adjustable with respect to each other or can be constructed as a unitary part. The plurality of needles 166 can be coated with anti-oxidant or other skin nutrient. Additionally, a liquid-soluble material could be embedded in the surface of the needles 166. As shown in FIG. 4, an embodiment of the tip 160 can have one or more fluid delivery points 144 and one or more suction points 142. FIG. 4A shows an embodiment of the tip 160 where there is a single fluid delivery point 144 and a single suction point 142.

Figure 5:
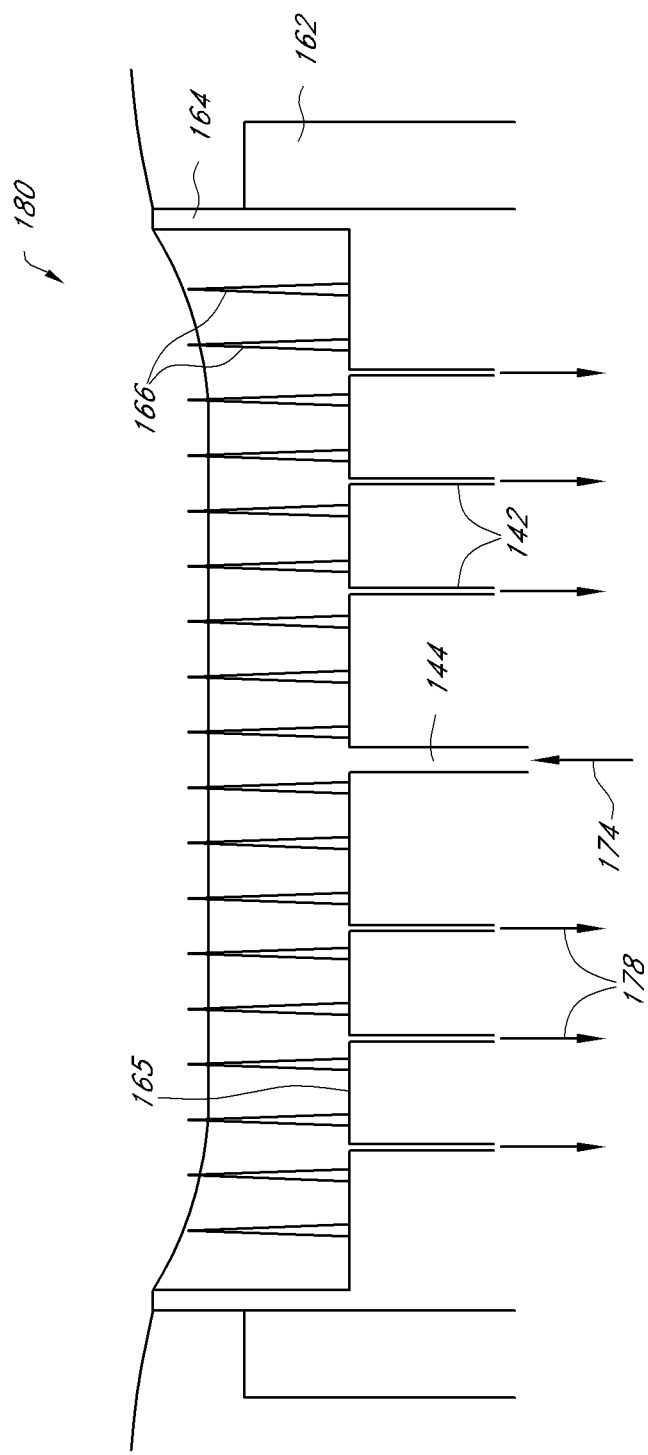
FIG. 5 is the same view from FIG. 4 where the needles are penetrating the skin of a patient.

In some embodiments, when the tip 160 is applied to the skin 180 of a patient, suction 178 generated though one or more suction points 142 on the tip can pull the skin 180 onto the plurality of needles 166, as shown in FIG. 5. Contact between the skin 180 and the peripheral lip 164 can create a seal around the treated area of skin 180. The plurality of needles 166 can be sized and the suction 178 can be applied in such a way that the needles 166 penetrate the epidermal layer of the skin 180. During treatment, treatment fluids 174 can be delivered to the skin via one or more fluid delivery points 144. Waste and excess fluids can be removed from the treated area of skin 180 via the one or suction points 142. This treatment could occur before, during, after or in lieu of other microdermabrasion or other skin treatment procedures.

Figure 6:
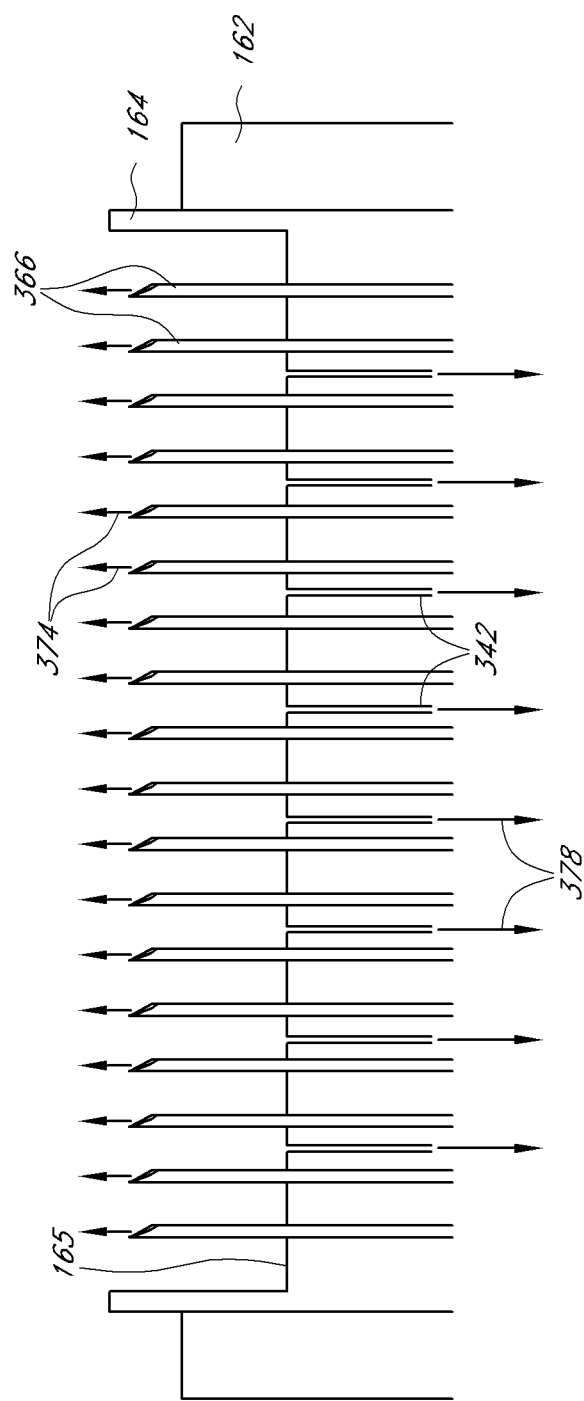
FIG. 6 is a cross-section view of an embodiment of the tip along cutting plane A-A of FIG. 3 showing hollow needles in fluid communication with a fluid delivery conduit.
Figure 6A:
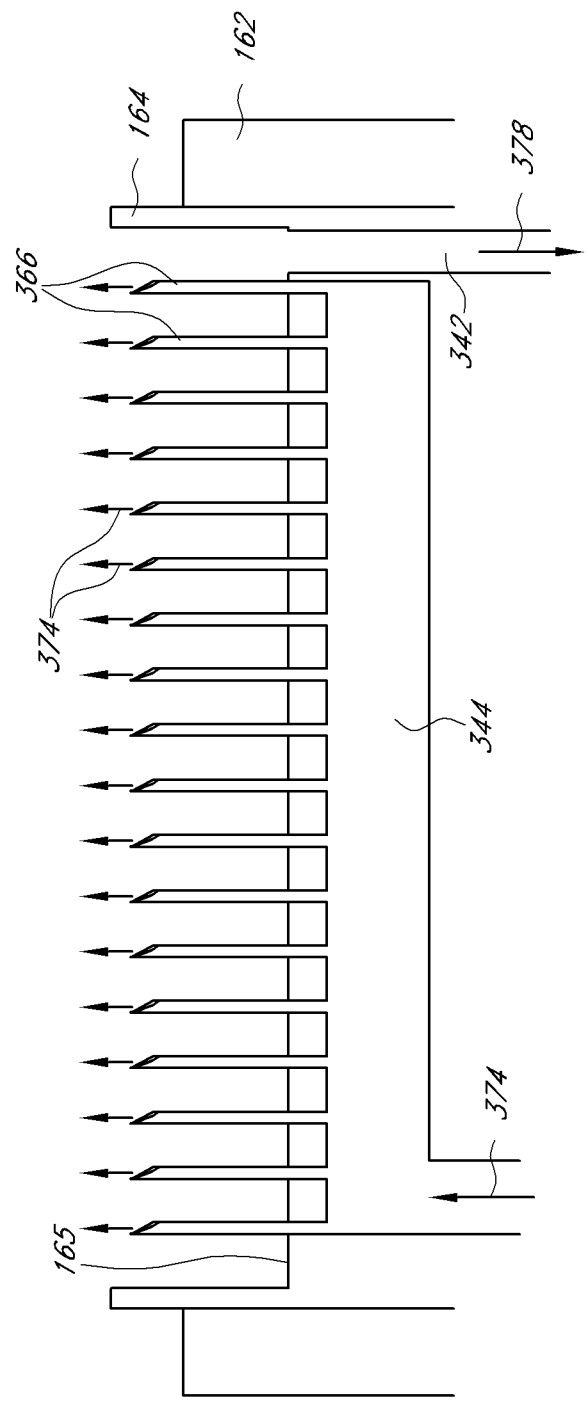
FIG. 6A is the same view as FIG. 6 showing a single fluid delivery conduit in fluid communication with the hollow needles.
Figure 7:
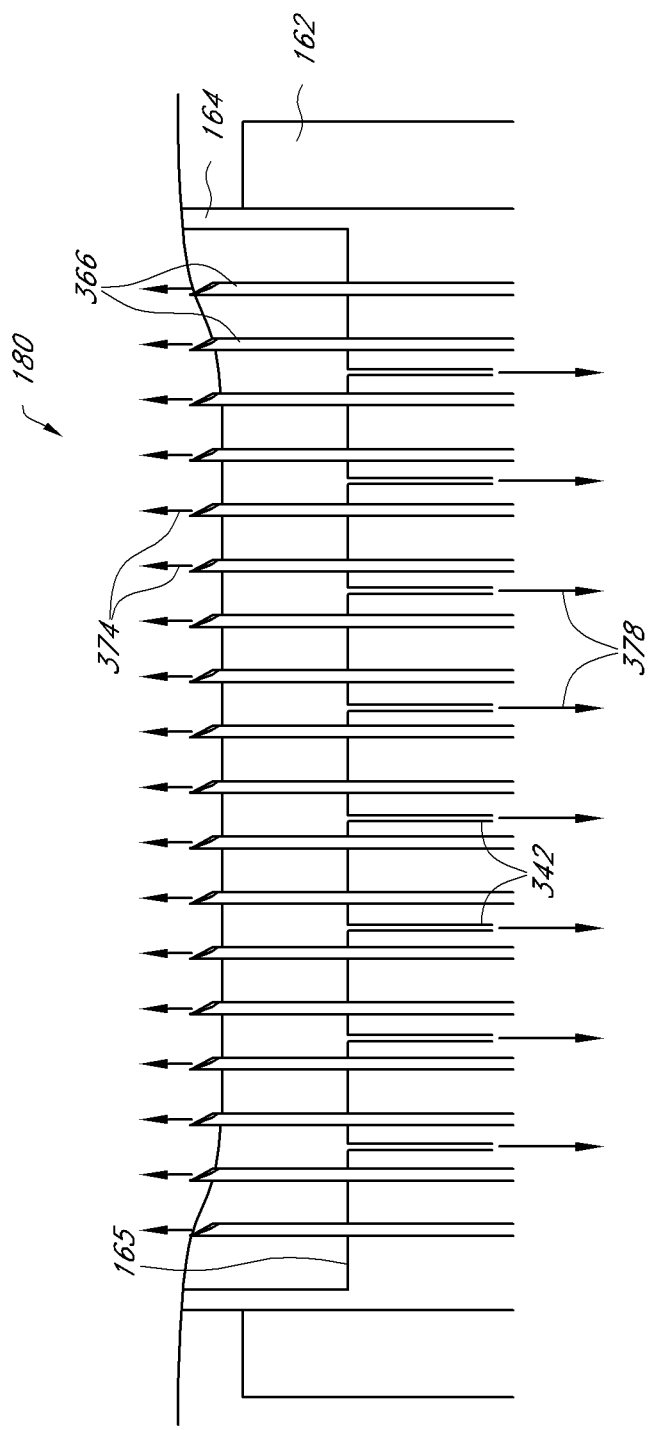
FIG. 7 is the same view from FIG. 6 where the needles are penetrating the skin of a patient.
Figure 8:
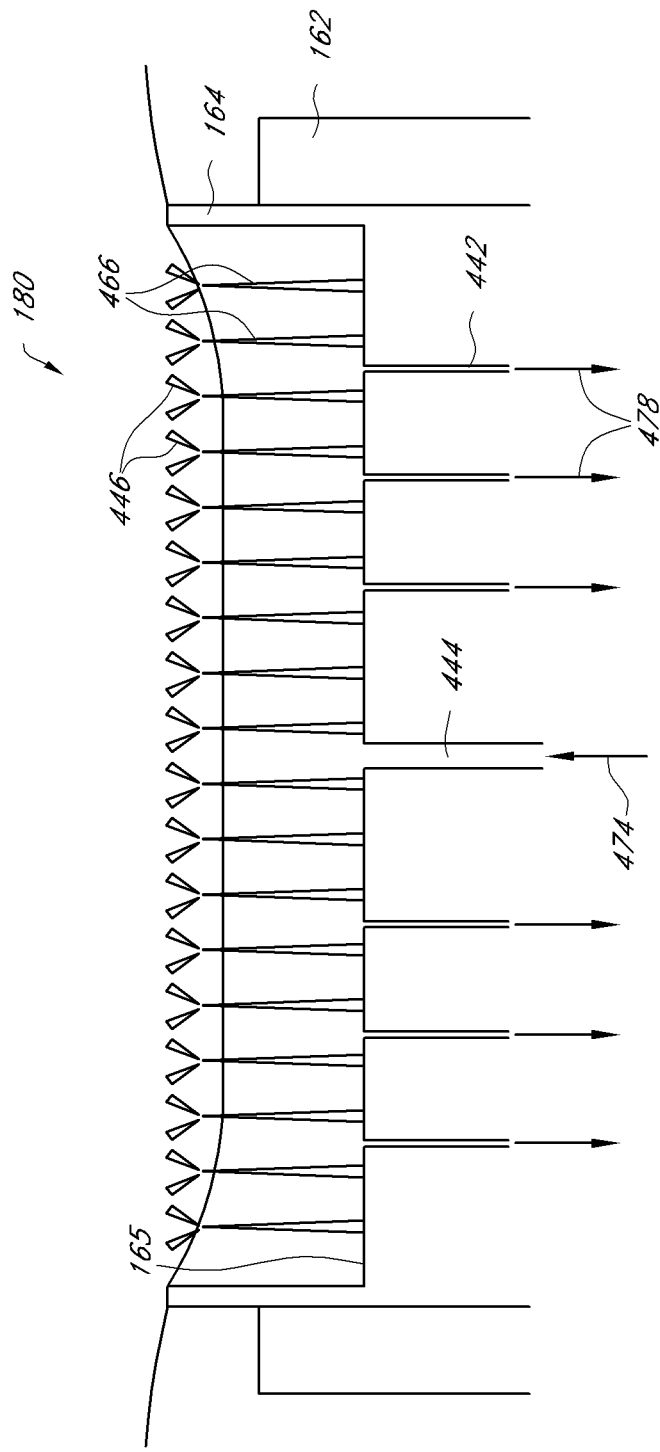
FIG. 8 is a cross-section view of an embodiment of the tip along cutting plane A-A of FIG. 3 showing the needles penetrating the skin of a patient and showing the needles emitting energy to the skin.

Hollow needles 366 can also be utilized for treatment of the skin, as shown in the embodiment of FIGS. 6-8. In a hollow needle embodiment, for example, treatment fluids 374 can be delivered at least partially into the skin 180 via hollow needles 366. The plurality of needles 366 can be coated with anti-oxidant or other skin nutrient. Additionally, a fluid-soluble material could be embedded in the surface of the needles 366. In some embodiments, one or more suction conduits 342 can provide suction 378 to assist in pulling the skin 180 onto the needles 366 and removing waste and/or excess fluids from the skin and/or the treatment surface. In addition, one or more fluid delivery points 344 can be placed in fluid communication with one or more of the hollow needles 366. Treatment fluids 374 can include, without limitation, liquids, dermal fillers, hot or cold vapors, gases and/or the like. By way of example, when delivering vapors and/or gases to the skin 180, one or more of the hollow needles 366 can be configured to penetrate into the secondary layer of the epidermis of the skin 180. The use of hollow needles 366 to treat the skin 180 can occur before, during, after or in lieu of other skin treatments, as desired or required.

The plurality of needles 466 can also be used to delivery energy 446 to the skin 180, as illustrated in FIG. 8. In some embodiments, energy 446 is delivered via hollow needles and/or solid needles. When delivering energy to the skin 180, one or more of the plurality of needles 466 can be configured to penetrate into the secondary layer of the epidermis of the skin 180. The source of the energy 446 can be radiofrequency (e.g. RF energy), microwave, ultrasound and/or any other source of energy 126 appropriate for treating the skin 180. Using energy 446 can at least partially damage the skin 180 and help trigger a beneficial healing or tissue repair response. Use of energy 446 to treat the skin 180 can be performed before, during, after or in lieu of other skin treatments.

Figure 9:
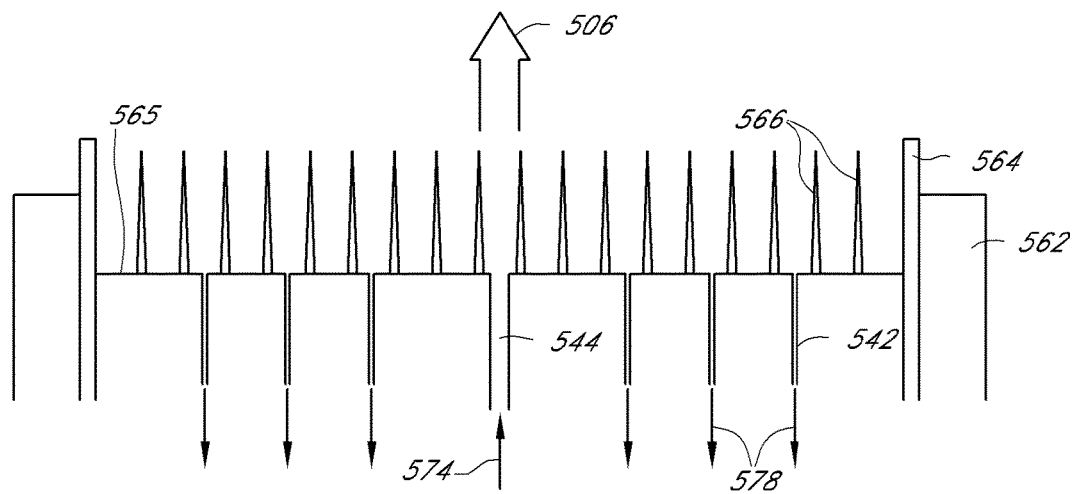
FIG. 9 is a cross-section view of an embodiment of the tip along cutting plane A-A of FIG. 3 showing a movable interior tip portion in two positions with respect to the peripheral lip of the tip.
Figure 9:
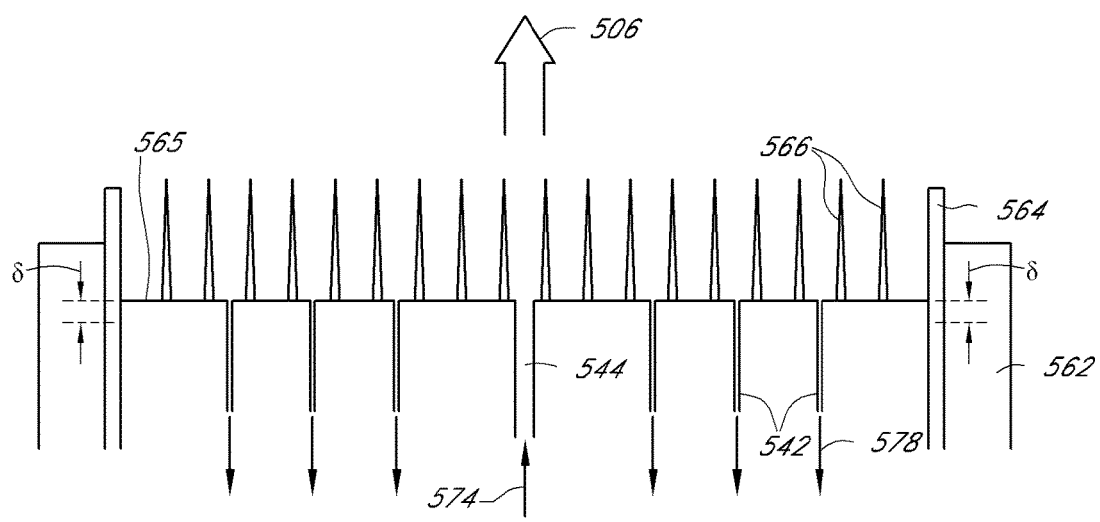

In addition to or in lieu of the use of suction 578 to pull the skin 180 onto a plurality of needles 566, the plurality of needles 566 and/or base member 565 can be moved with respect to the peripheral lip 564, as shown in FIG. 9. In an embodiment, a force 506 (e.g. pneumatic, mechanical, etc.) is used to move the plurality of needles 566 and/or base member 565 a distance δ with respect to the peripheral lip 564. The distance δ could be varied in order to achieve an optimal, adequate and/or preferred depth of penetration of the skin 180 by the needles 566. The force 506 can be used in combination with or instead of suction 578, and may be used with embodiments having hollow and/or solid needles 566. The force 506 can also be used in embodiments where energy 446 is delivered to the skin 180 via the plurality of needles 566.

In any of the embodiments disclosed herein, the tip, the handpiece assembly and/or any other component or device can include rigid and/or semi-rigid materials. For example, the tips can comprise one or more thermoplastics, other polymeric materials, rubbers, metals and/or the like. Accordingly, the tips can be manufactured using any suitable method, such as, for example, injection or compression molding, thermoforming, other molding methods, casting and/or the like. The tips can be disposable so that they are used once or only for a limited number of times. Alternatively, the tips can be reused. Therefore, in such embodiments, the tips are preferably configured to withstand the required cleaning, sterilizing and/or disinfecting procedures to which they may be exposed. In addition, any of the tips disclosed herein, either directly or by reference, can be used in wet and/or dry systems. In general, wet systems include skin treatment devices, assemblies or systems in which serums, other fluids and/or other materials are conveyed to the tip during the procedure. On the other hand, dry systems include skin treatment devices, assemblies or systems in which serums, other fluids and/or other materials are generally not conveyed to the tip during the procedure.

As discussed, one or more fluids or other substances can be delivered to the tip of a handpiece assembly during a skin treatment procedure. In some embodiments, such fluids and/or other materials can be stored within a cartridge that is secured to the handpiece assembly. Alternatively, these fluids and/or other materials can be stored in a canister or other container that is separate from the handpiece assembly. In such arrangements, as discussed herein, the handpiece assembly can be placed in fluid communication with one or more containers using conduits or other fluid lines.

In some embodiments, human growth factors, cytokines, soluble collagen, antioxidants, hyaluronic acid, matrix proteins, other proteins, serums, water, saline, other fluids and/or other materials can be delivered to the skin during a treatment procedure. Such materials can be delivered individually or as part of a mixture. Such materials or combination of materials can be provided in a cartridge or other container, which, as discussed, can be placed in fluid communication with a handpiece assembly. These treatment fluids and other materials, either alone or in combination, can help reduce the appearance of wrinkles, fine lines, age spots, scarring and/or other skin conditions. In addition, such fluids and/or other materials can help to reduce skin roughness, to rejuvenate the skin and/or improve skin texture. Further, such fluids or other treatment materials can provide one or more other therapeutic, aesthetic or other benefits to a user's skin.

In any of the embodiments described and/or illustrated herein, or variations thereof, treatment fluids and/or other materials can be delivered to the tip of a handpiece assembly using one or more ways. For example, in some embodiments, serums or other substances can be delivered through a vial, cartridge, supply canister, fluid bottle (e.g., included in a larger manifold or multiple fluid distribution system) and/or the like. Such serums, compositions, other fluids or substances can be pre-mixed so that they are delivered to the tip and the skin unmodified or substantially unmodified.

In other embodiments, serums, fluids, gels or other materials can be in the form of a pack container dry granular material, viscous gels and/or the like. Such packs can be mixed with water or some other fluid by a user to a desired concentration. In other embodiments, one or more treatment materials can be impregnated or otherwise embedded into the tips of the handpiece assemblies. Thus, such materials (e.g., powders, solids, gels, etc.) can advantageously dissolve when they contact water, saline or some other liquid. In still other embodiments, the treatment materials can be contained within a capsule, tablet or other enclosure. Such enclosures can be configured to dissolve when placed in water or some other fluid. Therefore, a user may be required to place a capsule, the contents of a pack or some other materials into a cartridge, canister or other container and add water, saline or other fluid before use.

In some embodiments, one or more serums or other substances can be delivered to the treatment surface of a handpiece assembly to treat a particular skin condition. For example, the system can be used to treat acne, dry or oily skin, fine lines, sun-damaged skin, other skin diseases or disorders and/or like.

In some embodiments, the serums, other materials and/or a combination of such serums or other materials can be utilized for the treatment of substantially most or all skin types. For example, such serums and/or other materials can be used when the handpiece assembly exfoliates skin.

In another embodiment, the serums, other materials and/or or a combination of such serums or other materials can be used during a follow-up (e.g., secondary, tertiary, etc.) or finish treatment step. For example, such serums and/or other materials can be used to hydrate the skin and/or lighten treat skin damage, either in lieu of or in addition to exfoliating skin. In such embodiments, the serums and/or other materials can comprise human growth factors, cytokines, soluble collagen, matrix proteins, other proteins, anti-oxidants, hyaluronic acid and/or the like.

In yet other embodiments, the serums, other materials and/or a combination of such serums or other materials can be used to target acne or oily skin conditions. Other serums, other materials and/or combinations of such serums or other materials can be used to target one or more types of skin conditions or treatments. Further, a particular treatment procedure can include or use one, two or more of such serums or other materials during various treatment phases (e.g., exfoliation, finish or polishing treatment, post-treatment, etc.).

In some embodiments, one or more kits can be developed that target a specific type of user, skin condition, desired result and/or the like. For example, such a kit can comprise serums and/or other materials that target teenage acne. As discussed, the serums and/or other materials contained in such kits can be in one or more different forms, such as, for example, liquids, gels, other fluids, powders, solids and/or the like. In some embodiments, such serums and/or other materials can be configured for immediate use. Alternatively, a particular amount of water, saline or other liquids, other dilution or dissolving agents and/or the like may need to be added to the serums and/or other materials to get them to a usable state. Kits can include one or more cartridges or other containers that are configured to be placed onto and removed from a handpiece assembly as discussed herein.

In addition, depending on who the target user is (e.g., teenagers, adults, etc.) and/or how severe a particular condition is, the concentration or strength of the serums and/or other materials can be varied. For example, for younger users, a kit directed at acne treatment can comprise lower concentrations of serums and/or other materials. By way of another example, kits comprising higher concentrations or strengths of serums and/or other materials can be used to treat oily skin or acne in adults. In another embodiment, a kit can be developed to target users whose skin is generally typical (e.g., the users' skin is not abnormally dry or oily, the users do not have excessive amount of acne or scarring, etc.).

As discussed, the kits can include one, two or more different types of treatment combinations. For example, a kit can comprise a first combination of serum(s) and/or other material(s) that is intended to target the exfoliation of skin. The same kit may include a second treatment combination that can be used in a follow-up treatment to treat oily skin or the like. In other embodiments, however, a kit can comprise more or fewer treatment combinations, as desired or required by a particular skin treatment procedure.

The systems, apparatuses, devices and/or other articles disclosed herein may be formed through any suitable means. The various methods and techniques described above provide a number of ways to carry out the various concepts disclosed herein. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments disclosed herein. Similarly, the various features and steps discussed above, as well as other known equivalents for each such feature or step, can be mixed and matched by one of ordinary skill in this art to perform methods in accordance with principles described herein. Additionally, the methods which are described and illustrated herein are not limited to the exact sequence of acts described, nor are they necessarily limited to the practice of all of the acts set forth. Other sequences of events or acts, or less than all of the events, or simultaneous occurrence of the events, may be utilized in practicing the embodiments disclosed herein.

Although the certain concepts have been disclosed in the context of certain embodiments and examples, it will be understood by those skilled in the art that the scope of the concepts disclosed herein extends beyond the specifically disclosed embodiments to other alternative embodiments and/or uses and obvious modifications and equivalents thereof.

What is claimed is:

1. A device for treating the skin, the device comprising:
a handpiece assembly having a first end and a second end, the handpiece assembly comprising a fluid delivery conduit and a suction conduit, the suction conduit being configured to be in fluid communication with a suction source; and
a tip positioned along the first end of the handpiece assembly, the tip being configured to contact the skin, the tip comprising:
a base member;
a peripheral lip, a top of the peripheral lip defining a distal end configured to contact the skin during use,
a first opening in the base member in fluid communication with the fluid delivery conduit,
a second opening in the base member in fluid communication with the suction conduit, and
a plurality of needles extending from the base member;
wherein the base, and thus the first and second openings, are recessed relative to the top of the peripheral lip and the distal end;
wherein an interior tip region is defined by the peripheral lip and the base member;
wherein the first opening is configured to be in constant fluid communication with the second opening during use;
wherein the suction conduit is in constant fluid communication with the second opening of the tip to ensure that suction is maintained along the second opening when the device is in use; and
wherein, when the suction conduit is in fluid communication with a suction source and when the suction source is activated, the tip is configured to draw skin toward the needles, within the interior tip region; and
wherein the base member and the needles of the tip are movable relative to the peripheral lip.

2. The device of claim 1, wherein a fluid delivered through the fluid delivery conduit is a liquid, vapor, or gas.

3. The device of claim 1, wherein the tip is selectively removable from the handpiece assembly.

4. The device of claim 1, wherein the needles are coated with an anti-oxidant or other skin nutrient.

5. The device of claim 1, wherein a fluid-soluble material is positioned along a surface of the needles.

6. The device of claim 1, wherein the base member and the needles are movable relative to the peripheral lip mechanically or pneumatically.

7. The device of claim 1, wherein the handpiece assembly comprises an energy delivery device or an energy input.

8. The device of claim 7, wherein a source of energy for the energy delivery device or the energy input comprises at least one of radio frequency, microwave, and ultrasound.

9. The device of claim 1, wherein energy is introduced to the plurality of needles via an energy input.

10. A method for treating the skin of a subject, the method comprising:
   placing a tip of a skin treatment device against a portion of the skin of a subject, the skin treatment device comprising a handpiece assembly, wherein the tip is secured to a distal end of the handpiece assembly;
   wherein the tip comprises a plurality of needles configured to engage and penetrate the skin, wherein each of the needles extends from a base of the tip and comprises a needle end, the tip further comprising a peripheral lip;
   wherein the tip comprises at least one suction opening, the at least one suction opening being configured to be in constant fluid communication with a suction conduit of the handpiece assembly;
   wherein the tip comprises at least one fluid delivery opening, the at least one fluid delivery opening being in fluid communication with a fluid delivery conduit of the handpiece assembly;
   wherein placing the tip against a portion of the skin of a subject comprises contacting the peripheral lip of the tip against the subject's skin;
   activating a suction force in fluid communication with the suction conduit of the handpiece assembly, wherein activating the suction force creates a suction along the tip and within an interior cavity of the tip, wherein the interior cavity of the tip is defined by the peripheral lip and the base of the tip;
   delivering at least one treatment material to the tip via the fluid delivery conduit and the at least one fluid delivery opening, wherein the at least one treatment material is continuously delivered to the tip during use since the at least one fluid delivery opening is recessed relative to the needle end of each of the needles;
   drawing skin of a subject within the interior cavity of the tip to cause the needles to penetrate skin of the subject; and
   wherein activating the suction force results in removing spent treatment material away from the tip.

11. The method of claim 10, further comprising moving the base and the tip relative to the peripheral lip of the tip to further control the movement of the needles relative to skin of a subject.

12. The method of claim 11, wherein the base and the needles are moved relative to the peripheral lip mechanically.

13. The method of claim 10, wherein the base and the needles are moved relative to the peripheral lip pneumatically.

14. The method of claim 10, further comprising delivering energy to the skin of the subject.

15. The method of claim 14, wherein the energy comprises at least one of radio frequency, microwave and ultrasound.

16. The method of claim 10, wherein the at least one treatment material comprises at least one of the following: cytokines, soluble collagen, antioxidants, matrix proteins and human growth factors.

17. The method of claim 10, wherein the at least one treatment material comprises a growth factor.

* * * * *